(12) United States Patent
Smith

(10) Patent No.: US 6,540,699 B1
(45) Date of Patent: Apr. 1, 2003

(54) SYSTEM FOR INCORPORATING SONOMICROMETER FUNCTIONS INTO MEDICAL INSTRUMENTS AND IMPLANTABLE BIOMEDICAL DEVICES

(75) Inventor: Wayne L. Smith, Ontario (CA)

(73) Assignee: Sonometrics Corporation, Ontario (CA)

( * ) Notice: Subject to any disclaimer, the term of this patent is extended or adjusted under 35 U.S.C. 154(b) by 0 days.

(21) Appl. No.: 09/807,229

(22) Filed: Apr. 9, 2001

Related U.S. Application Data
(60) Provisional application No. 60/147,703, filed on Aug. 6, 1999, and provisional application No. 60/134,746, filed on May 18, 1999.

(51) Int. Cl.⁷ .............................................. A61B 5/117
(52) U.S. Cl. ....................... 600/587; 600/498; 600/508; 607/9; 607/23
(58) Field of Search ................................. 600/437, 443, 600/481, 498, 506, 508, 587; 607/9, 23

(56) References Cited

U.S. PATENT DOCUMENTS

| 4,109,644 A | 8/1978 | Kojima ........................... 128/2 |
| 4,936,304 A | 6/1990 | Kresh et al. ................. 128/419 |
| 4,993,427 A | 2/1991 | Barr et al. ................... 128/774 |
| 5,156,154 A | 10/1992 | Valenta, Jr. et al. .... 128/661.09 |
| 5,305,745 A | 4/1994 | Zacouto ....................... 128/637 |
| 5,538,007 A | * 7/1996 | Gorman ....................... 128/710 |
| 5,797,849 A | 8/1998 | Vesely et al. ................ 600/461 |
| 5,817,022 A | * 10/1998 | Vesely ......................... 600/443 |
| 5,928,131 A | 7/1999 | Prem ............................ 600/16 |

FOREIGN PATENT DOCUMENTS

| EP | 467 695 | 1/1992 |
| EP | 536 873 | 4/1993 |
| WO | 99/07285 | 2/1999 |

* cited by examiner

Primary Examiner—Henry C. Yuen
Assistant Examiner—Johnny H. Hoang
(74) Attorney, Agent, or Firm—Arter & Hadden LLP

(57) ABSTRACT

A biomedical apparatus is disclosed including an implantable biomedical device for providing biomedical assistance to the body structure and a device controller for regulating the operation of the biomedical device. A sonomicrometer arrangement is provided, in contact with the body structure and in communication with the device controller. The sonomicrometer arrangement ultrasonically measures at least one physical parameter of the body structure and provides feedback information to the device controller. The device controller then regulates the operation of the biomedical device in response to the feedback information.

19 Claims, 4 Drawing Sheets

SYSTEM FOR INCORPORATING SONOMICROMETER FUNCTIONS INTO MEDICAL INSTRUMENTS AND IMPLANTABLE BIOMEDICAL DEVICES

CROSS REFERENCES TO RELATED U.S. APPLICATIONS

This application claims the benefit of U.S. Provisional Application No. 60/134,746, filed May 18, 1999, and U.S. Provisional Application No. 60/147,703, filed Aug. 6, 1999.

FIELD OF INVENTION

The present invention generally relates to enhanced implantable biomedical devices and instruments, and more particularly to implantable biomedical devices and instruments having sonomicrometer functions incorporated therein.

BACKGROUND OF THE INVENTION

Using the time-of-flight principle of high frequency sound waves, it is possible to accurately measure distances within an aqueous medium, such as inside the body of a living being. High frequency sound, or ultrasound, is defined as vibrational energy that ranges in frequency from 100 KHz to 10 MHz. The device used to obtain dimensional measurements using sound waves is known as a "sonomicrometer". A typical sonomicrometer uses two or more piezoelectric transducers that act as transmitters and receivers of ultrasound energy when situated in a sound-conducting medium and connected to electronic circuitry. The distance between transducers is measured by first electrically energizing the transmitting transducer, causing it to produce ultrasound energy. The resulting sound wave then propagates through the medium until it is detected by the receiving transducer. The propagation time of the ultrasound signal, when multiplied by the velocity of sound in the medium, yields the distance between transducers.

The transducers typically take the form of a piezoelectric ceramic (e.g., PZT or PVDF material) that are energized by a voltage spike, or impulse function of a designated duration. This causes the transducer to oscillate at a characteristic resonant frequency that results in a transmitted signal which propagates away from the transmitter through the medium.

The receiver detects the sound energy produced by the transmitter and begins to vibrate in response thereto. This vibration produces an electronic signal on the order of millivolts that can be amplified by appropriate receiver circuitry.

The propagation velocity of ultrasound in many materials is well documented. The distance traveled by a pulse of ultrasound can therefore be measured simply by recording the time delay between the instant the sound is transmitted and when it is received. This process of transmission and reception can be repeated many times per second. Depending on the embodiment, a large matrix of distances between many transducers can be obtained. In U.S. Pat. Nos. 5,515,853; 5,795,298; and 5,797,849 (fully incorporated herein by reference), a procedure is explained for determining the spatial {x,y,z} coordinates for each transducer from the distance matrix.

Presently, there are several classes of biomedical devices that perform electrical or mechanical activity within the body that do not incorporate dimension-measurement technology as part of their operation. It is believed that the absence of this technology is due to the lack of awareness of sonomicrometry by biomedical engineers, leading to a low appreciation of the utility and benefits of sonomicrometry.

The present invention addresses the foregoing problem, as well as others, to provide implantable biomedical devices which collect dimension-measurement data using sonomicrometer technology.

SUMMARY OF THE INVENTION

According to the present invention there is provided an implantable biomedical device which uses sonomicrometry to provide dimension-measurement data that enhances the functionality of the biomedical device.

An advantage of the present invention is the provision of a cardiac pacemaker which is capable of acquiring cardiac dimensional data and calculating from that data parameters such as heart rate, contractile amplitude, contractility, cardiac size, stroke volume and ventricular ejection fraction.

Another advantage of the present invention is the provision of a cardiac defibrillator which is capable of acquiring cardiac dimensional data and calculating from that data parameters such as heart rate, contractile amplitude, contractility, cardiac size, stroke volume and ejection fraction, wherein the cardiac dimensional data and/or computed parameters may be used to determine the need to apply a defibrillation shock, and/or optionally to evaluate post-shock cardiac contractility.

Still another advantage of the present invention is the provision of a ventricular assist device which is capable of acquiring cardiac dimensional data and computed parameters that provide feedback and control information, wherein the information is suitable for determining the appropriate or optimal interaction between the heart and assist device. The nature of this interaction could, for example, pertain to ventricular size, filling or ejection rate, or cardiac output.

Yet another advantage of the present invention is the provision of a post-operative cardiac monitoring device which is capable of acquiring cardiac dimensional data, wall thickness data, and computed parameters such as heart rate, contractile amplitude, contractility, cardiac size, stroke volume and ejection fraction, wherein the cardiac dimensional data and computed parameters can be used to adjust drug doses and treatment protocols during recovery, and to evaluate cardiac function.

These advantages and others are provided by the biomedical apparatus of the present invention in which an implantable biomedical device is provided for providing biomedical assistance to a body structure, and including a device controller for regulating the operating of the biomedical device.

A sonomicrometer arrangement is provided, in contact with the body structure and in communication with the device controller. This sonomicrometer arrangement ultrasonically measures at least one physical parameter of the body structure and provides feedback information to the device controller. The device controller regulates the operation of the biomedical device in response to the feedback information.

Still other advantages of the invention will become apparent to those skilled in the art upon a reading and understanding of the following detailed description, accompanying drawings and appended claims.

DETAILED DESCRIPTION OF THE PREFERRED EMBODIMENT

In accordance with the present invention, sonomicrometer technology (e.g., dimension-measurement transducers and circuitry) is incorporated into implantable biomedical devices. By using dimension-measurement data (e.g., cardiac dimensions, rate of contraction, etc.), the operations of the device are improved (e.g., device control). For instance, defibrillation, rather than pacing, may be implemented based on the presence or absence of contraction in a cardiac muscle. Currently, these conditions are detected electrically, but a mechanical input provides additional information that would be incorporated into a decision tree for the implanted device.

It should be appreciated that while the present invention will be described with particular reference to pacemakers, implantable defibrillators, ventricular assist devices, and post-operative cardiac monitoring methods, the present invention is also applicable to other implantable biomedical devices to provide a sonomicrometer-based dimension-measurement data collection and evaluation system.

Figure 1A:
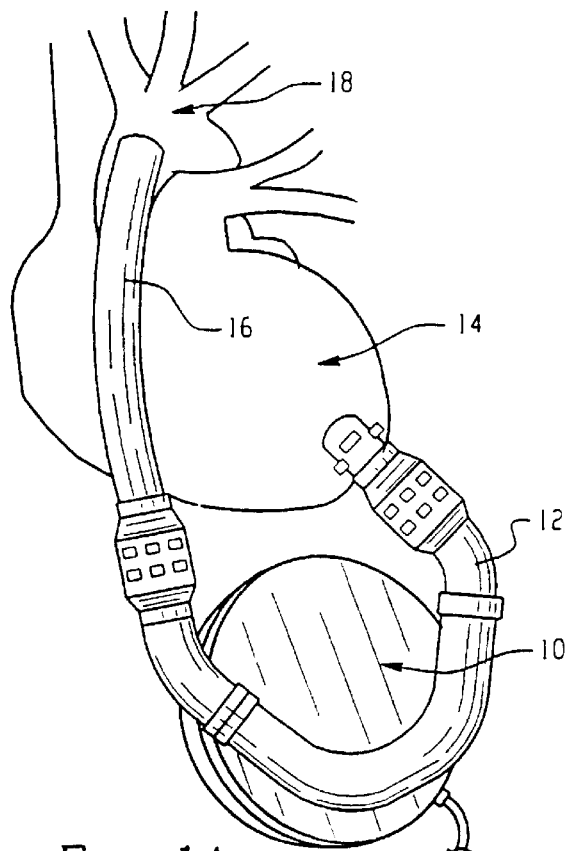
FIGS. 1A, 1B, 1C and 1D depict typical ventricular assist devices (VADS).
Figure 1C:
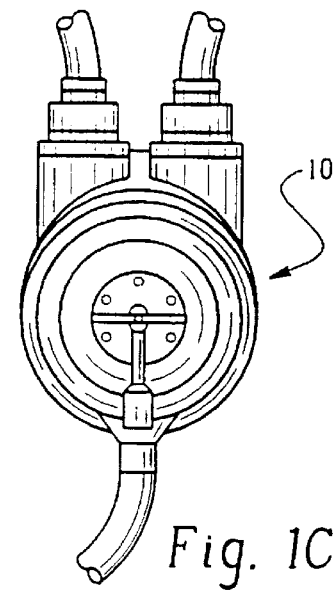
Figure 1B:
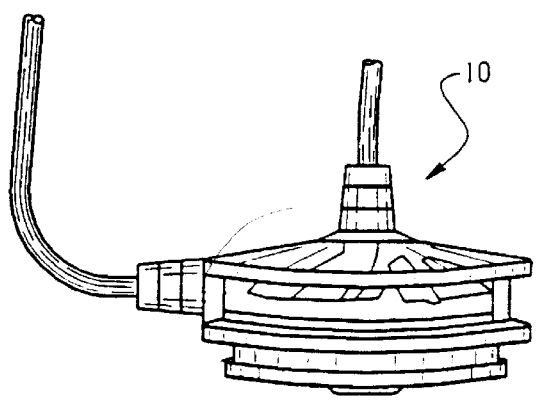
Figure 1D:
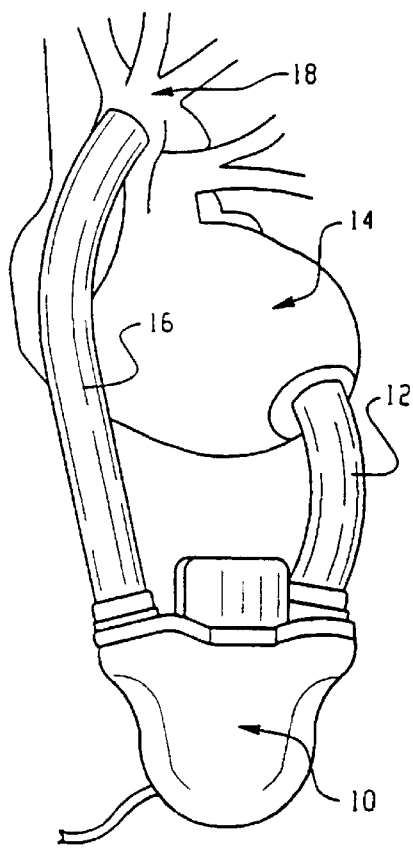

A. Inclusion of Dimension Measurement Capability in Ventricular Assist Devices Ventricular Assist Devices or VADs (most commonly Left Ventricular Assist Devices or LVADs) perform auxiliary pumping support for the heart by filling the ventricles more completely prior to ventricular systole or by replacing partially or completely the pumping effort of the ventricles. The cardiac dimensional data and computed parameters noted above may be used to provide feedback and control information. This information is suitable for determining, among other items, the appropriate time to stop pumping blood into the ventricles because they have reached a predetermined size. As shown in FIGS. 1A–1D, ventricular assist pumps are typically impellers (FIGS. 1A and 1B) or diaphragms (FIGS. 1C and 1D). They can also be in the form of bladders or bands that inflate under pressure and squeeze the blood chamber that they surround (not shown). In any case, a typical VAD includes a blood pump 10 that includes an inflow 12 that draws blood from the left ventricle 14 of the heart, and pumps the blood through an outflow 16 into the aorta 18 and out into the body.

Previous-type VADs produce problems known in the literature as pump-induced "ventricular collapse" and also "hyperdilation." The VAD must withdraw blood from one vessel or chamber in or near the heart and eject this blood into a different chamber or vessel in or near the heart, thereby completing the circulation of blood by bypassing a diseased or non-functional portion of the natural heart. The flow of blood through the body and it's return to the inflow region of the VAD is variable and during periods of insufficient return the VAD's pumping action can collapse the chamber or even the vessel of the inflow region. Another aspect of operation of the VAD is that again due to changes in the blood flow in the body the vessel or chamber that is receiving blood from the outflow of the VAD may expand beyond desired limits, resulting in hyperdilation of the heart chamber or vasculature.

The problem of vascular or chamber collapse or hyperdilation is the result of the VAD being instructed to pump more blood than the current conditions of the vasculature can support or tolerate. When this occurs the controlling mechanism of the VAD must reduce the pumping activity of the VAD. The variability of the patient's vasculature or the patient's activity level is the root cause of the need to vary the pumping function of the VAD so as not to cause a condition of collapse or hyperdilation.

Some previous-type devices use ultrasonic or electromagnetic flow sensors that provide some VAD's with the feedback necessary to maintain the desired blood flow to support life and even ambulatory activity, but these sensors do not measure the extent of vascular collapse or hyperdilation. The use of pressure transducers to measure the pressure in the inflow and outflow region of the VAD are extrapolated to give indications of collapse or hyperdilation because it is intuitive that a high pressure will lead to expansion or dilation. However, in reality the muscle walls of the ventricles and vasculature do not have constant material properties so a direct pressure-volume relationship can not be assumed.

Pressure transducers have commonly been used to solve this problem because of their ubiquitous nature in the biomedical engineering field. However, pressure transducers have a history of drift and attenuated readings when exposed to the natural fiberotic processes of the body over time. The method of direct measurement using sonomicrometers would be preferred since their sensitivity and accuracy does not diminish over time.

An extremely precise measure of the inflow and outflow quantities can theoretically lead to the determination that a flow imbalance is occurring or is about to occur, but even the smallest error in such flow measurements are integrated over time resulting in a feedback mechanism governed by faulty information. Pressure transducers are vulnerable to fibrotic processes that reduce their ability to directly sense the chamber or vascular pressure in question, and their use necessitates that they be placed in the blood stream, which is a surgical complication as well as a thrombolytic risk to the patient. Strain gauges are an alternative way to measure the degree of stretch of a vascular or ventricular structure, but they have a limited range of function and only give measures of relative changes in size. They can also suffer from long-term drift.

Also, the sensation of pressure in the inflow and outflow vessel or ventricle does not give an accurate indication of the degree of collapse or dilation of the vessel or ventricle. Because of this, optimal matching of the inflow and outflow conditions can not be obtained over the wide range of pumping functions required, for example, during outpatient ambulatory activity. The conditions of collapse and hyperdilation can stress or damage the heart muscle, creating a situation that is counter-productive to the overall goal of VAD therapy, which in some cases is to allow a failing heart to regenerate.

Figure 2:
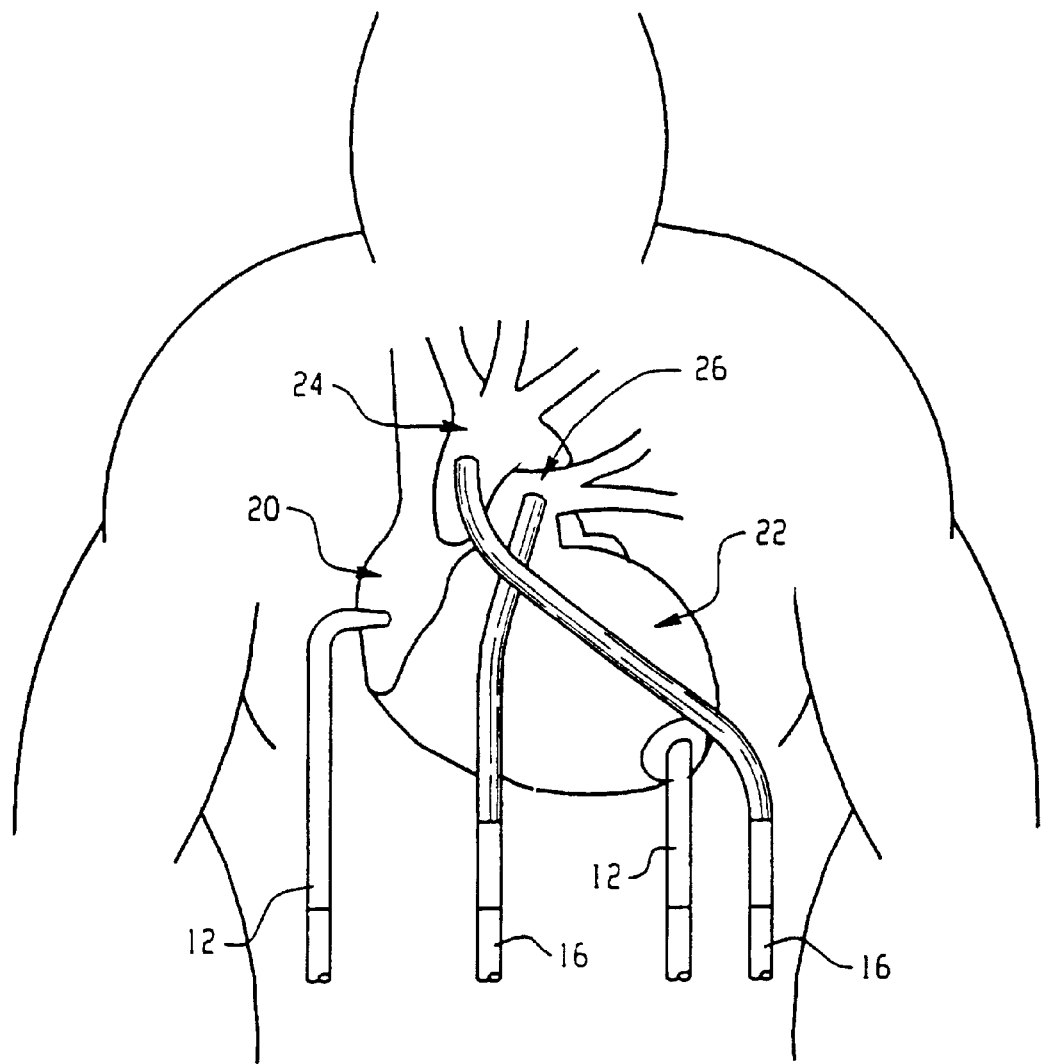
FIG. 2 shows the typical connections made to the heart in a VAD to provide bi-ventricular support.

The VAD also has inflow and outflow orifices or ports 20, 22, 24, 26 which are directly sewn into specific sites on the heart or the great vessels which come directly off the heart as shown in FIG. 2 for bi-ventricular support. These sites are typically the right atrium 22, the left ventricle 24 (usually the apex), the proximal aorta 24 (usually not above the ascending arch), and the proximal pulmonary artery 26. FIG. 2 shows these sites and the conduits which lead from them to the pumping device. All of these sites and vascular structures are compliant and are also susceptible to damage should they be distended or dilated due to over-filling by the artificial pump. Also, they are as susceptible to collapse leading to the cessation of blood flow if blood is withdrawn from them too quickly. Thus, increased VAD operation can also damage these components.

As is accomplished by the present invention, the addition of sonomicrometer technology allows for the direct measurement of the size of the inflow and outflow regions (be they vessels or chambers) and this information would be used as part of a feedback or control process to regulate the pumping action of the VAD. The present invention is applicable to all types of such devices by providing size, shape, area or volume information on the chamber or vessel they are withdrawing blood from or ejecting blood into. Specifically as used with a bladder type VAD, an important aspect of its operation is that it squeezes it's respective blood chamber when that chamber is sufficiently filled with blood, rather than simply relying on a sensation of pressure within the chamber, which is not a reliable guarantee of sufficient filling. The present invention can monitor the size of the chamber with the appropriate algebraic combination of sonomicrometer length measurements resulting in an aggregate signal indicative of chamber volume. This signal would then be monitored by the VAD controller which would make a decision to activate the bladder when the volume has reached a pre-determined value.

In an exemplary embodiment of the invention, sonomicrometer functions are incorporated into a VAD. The sonomicrometer arrangement measures the distance between piezoelectric transducers by causing the transducers to send and receive pulses of ultrasound energy between each other. By measuring the transit-time of these pulses through an interposing sound conducting material the distance between these transducers is determined. These transducers would be applied to the vascular or ventricular'structures that comprise the inflow and outflow regions connected to the VAD. This enables the continuous determination of size, area, and volume of these structures. These measurements are then incorporated into the control process of the VAD as.it operates so as to prevent the occurrence of collapse or hyperdilation of the vascular or ventricular structure in question.

Figure 3:
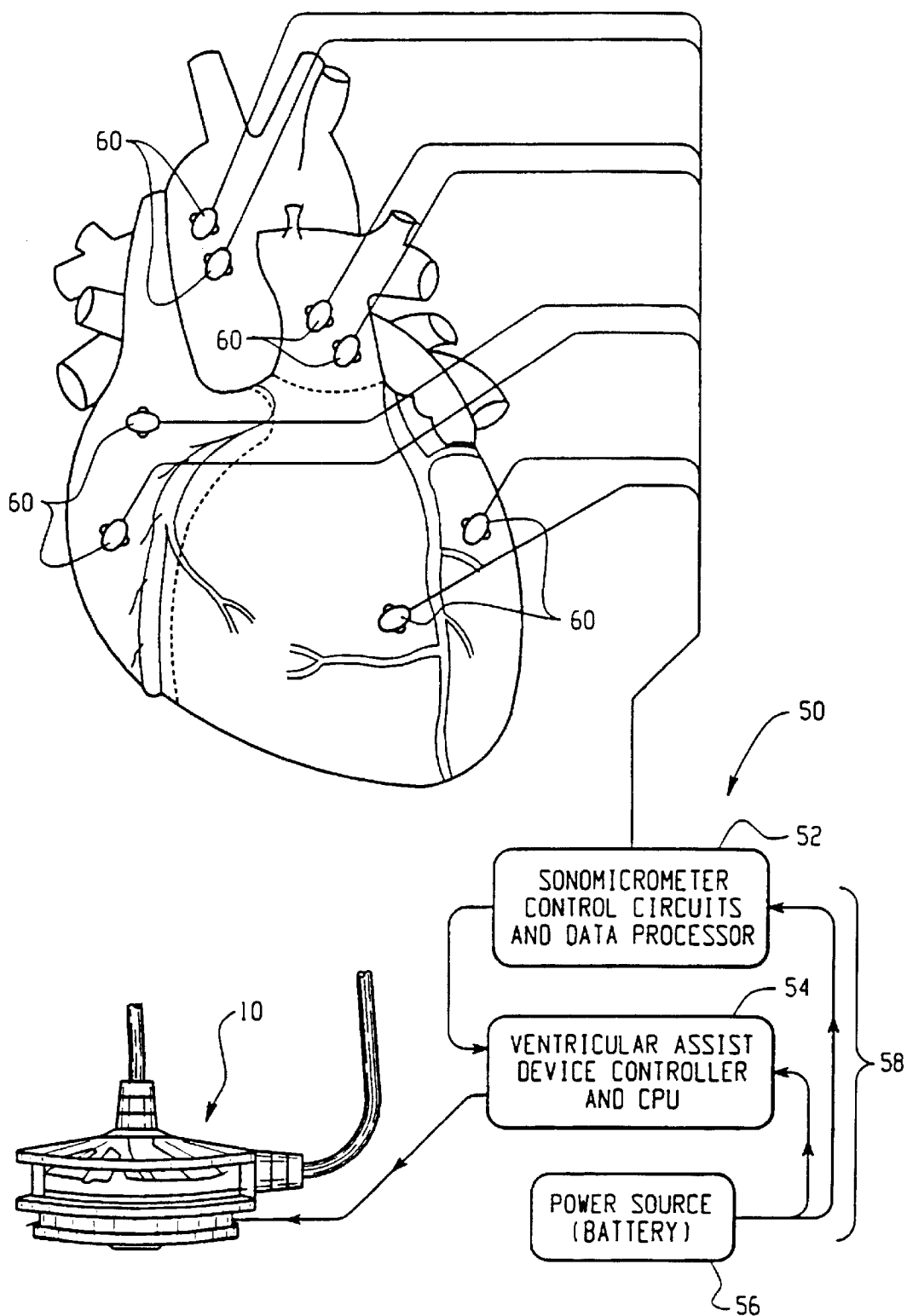
FIG. 3 is a diagram of a VAD incorporating the sonomicrometer arrangement of the present invention.

The exemplary embodiment of the present invention is depicted in FIG. 3, in which three separate functional modules are shown which may remain physically separate or be combined as desired to meet ergonomic or reliability or manufacturing criteria. The sonomicrometer 50 includes an associated sonomicrometer control and data processor 52 that performs dimensional measurements of the heart via ultrasonic transducers 54 which have been attached to relevant sites. (For clarity, the inflow and outflow conduits leading to the VAD pumps are not shown, but it should be appreciated that these conduits can be connected in any manner known to those skilled in the art.) FIG. 3 shows an approximate configuration for monitoring four inflow and outflow sites which are typical of bi-ventricular support. The number of ultrasound transducers can optionally be reduced if data from some sites is not required. Also, more than two transducers 60 can optionally be added to a given site in order to provide a more precise measure of area or volume of the relevant structure.

As also shown in FIG. 3, the sonomicrometer control 52 provides a control signal to a VAD controller 54 based on the sonomicrometer data. The VAD controller 54 regulates the operation of the pumping device 10 in such a way as to prevent relevant structures of the heart to not exceed pre-set (or adaptable) size or volume thresholds as reported by the sonomicrometer module, and in a likewise manner to prevent relevant structures to be reduced in size or volume to the point indicative of collapse. The VAD controller can be adapted to also take in data from other sensor types (not shown) such as pressure transducers or flow sensors, and the VAD controller can then be adapted to combine data from all sources to arrive at an integrated decision making process to control the pumping device.

The sonomicrometer control and data processor 52, along with VAD controller 54 and a power supply 56 (preferably a battery) are housed in an electronic module 58 suitable for implantation in the body or outside the body, as determined by necessity, ergonomics or practicality considerations. This housing can be made from metal alloys or plastic polyrners. Electrical connections to the housing are to be durable and fully sealed against the intrusion of body fluids and other contaminants. Provisions can be made for auxiliary data connections to allow changes to be made to the programming or functioning of this module by an external computer.

The electronics module 58 is provided for the sequential transmission and reception of ultrasound signals between the attached piezoelectric transducers 60. In the preferred embodiment, the micro-processor 52 runs an embedded program that controls the operation of the transducers 60. Additionally, in a preferred embodiment, this module is housed within the same enclosure as the VAD controller 60. The piezoelectric transducers 60 are connected via wires to the electronics module 58. The module 58 generates distance data in the form of digital or analog signals by causing the transducers to emit pulses of ultrasound while processing the received signals from non-transmitting transducers. Ultrasound signals in a range of between approximately 1–10 MHz with an amplitude in a range of between approximately 1–50 mV are communicated by receiving transducers to the module. Step-impulse signals on the order of several volts are sent to the transmitting transducers from the module.

During operation, the electronics module 58 causes the transducers 60 to sequentially emit pulses of ultrasound at a repetition rate from approximately 50 Hz to 500 Hz. Transducers 60 that are not emitting are instead receiving these acoustic pulses and the received signals are processed and converted to distance signals that are proportional to the distance between the given receiving transducer and the transmitting transducer.

The ultrasonic transducers 60 are configured to measure the physical dimensions of the heart or other body structure during operation of the device. In some of the contemplated embodiments of this invention, several such measurements are combined algebraically to derive a 2-dimensional area or 3-dimensional volume of the body structure. Any of these measurements, or their derivatives, can be further processed to yield the variation (maxima and minima) and rate of change of the heart or other body structure. For example, in one specific arrangement, three transducers 60 can be placed on the body structure to form a triangle, to measure the area enclosed by this triangle. In another specific arrangement, four transducers 60 can be used to model a cylindrical volume corresponding to the heart or other body structure, where the cylindrical volume has a cylindrical cross-section and a length. One pair of transducers 60 is taken to measure the circular cross-sectional diameter and the other pair is taken to measure the length of the cylinder. Of course, it will be appreciated that the transducers 60 can be varied in placement and in number to model any other desired geometrical shapes, such as would occur to those skilled in the art, without departing from the invention.

The distance signal derived from the transducers 60 may be conveyed as a digital unsigned quantity ranging from 8 to 16 bits wide, or it may be conveyed as a uni-polar analog voltage ranging from 0 (zero) to several volts in amplitude. The information provided above is used to determine if the size of measured structures are outside the desired range and, if so, to modify the pump action of the VAD so as to bring the size of these structures back to within the desired range.

Figure 4:
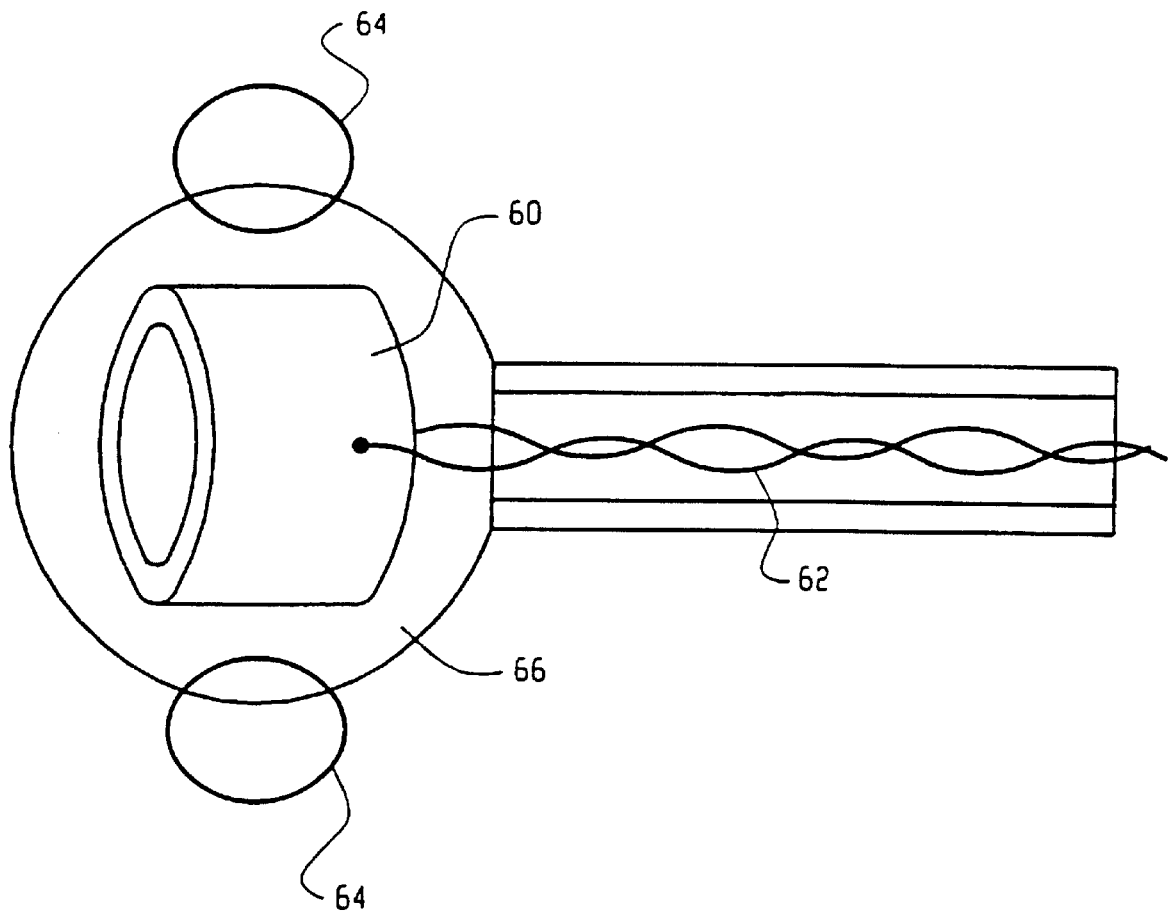
FIG. 4 is a detailed view showing a transducer of the sonomicrometer arrangement according to an exemplary embodiment of the invention.

The piezoelectric ultrasound transducers 60 can be constructed in a variety of ways, of cylindrical shape in the preferred embodiment. FIG. 4 shows the preferred embodiment of such a transducer 60. Signal wires 62 are bonded to-the inner and outer surface of the transducer 60. For durability purposes, these would be teflon-insulated multi-stranded stainless steel wires arranged as a twisted pair and covered in a silicone jacket. Also shown is a pair of attachment rings 64 for affixing to the surface of the heart, which would also be incorporated into an encapsulation material 66 surrounding the transducer. Other arrangements of attachment mechanisms are possible. The encapsulation material 66 is, biocompatible and may consist of injection-formed plastic or epoxy.

The piezoelectric transducers 60 can alternatively be flat or disk-shaped, fabricated from planar stock material, and can be approximately 1 to 2 mm, encapsulated in a material with long-term durability and biocompatiblity, such as Teflon™. Two signal wires and possibly a third shield wire will extend from these transducers in a flexible, durable, biocompatible cable and connect to an electronic sonomicrometer module. In this alternative embodiment, the two signal wires are made from 32 gauge stainless steel with a Teflon™ insulation arranged as a twisted pair. This pair is coated with a layer of silastic (silicone) with an over-all diameter of approximately 2 mm. A third wire (un-shielded) coil-wraps the twisted pair along it's entire length within the silastic coating. This cable terminates within an electronics control module. This module may be implanted inside the body, or alternatively may be positioned outside the body, in which case these cables will pass through a skin incision or through a connector device affixed to the skin surface.

The distance signals generated by the electronics module 58 are conveyed to the VAD controller 54. This conveyance can preferably be in the form of digital data transference on the data bus of the existing control assembly or in the form of an analog voltage signal that is sampled periodically by an Analog-to-Digital converter which is part of the control assembly or control computer.

The microprocessor operation code of the present invention is indicated as follows:

Code Inputs (Sonomicrometer Control Module):
  Number of crystals attached to the module;
  Desired data sampling frequency;
  List of dimensions to be output from the module;
  Miscellaneous parameters related to sonomicrometer function;
  Signals to reset the module or suspend it's operation.
Code Outputs (Sonomicrometer Module):
  distance data (in analog signal form via DAC or as numeric data);
  computed data (such as algebraic combinations of the distance data).
Sonomicrometer Module Microprocessor Code:
  This code takes input parameters and generates distance data or computed data by controlling the sequence of operation of ultrasonic transmission and reception hardware.

Code Inputs (VAD Controller):
  dimension or computed data from sonomicrometer module;
  physiological operating range of structures being measured.
Code Outputs (VAD Controller):
  A control signal (on/off, true/false, or variable control signal) used as a signal to regulate the pump operation of the VAD. If there are existing regulation signals then this control signal would be added in an appropriately weighed manner to these existing signals.
VAD Controller Code:
  The VAD controller 54 is an existing computational or control module designed specifically for it's intended type of VAD pump. Presumably it will always have a feedback process for the regulation of the pumping activity of the VAD, but it is beyond this invention to know how these feedback processes have been implemented.

Other benefits of this invention include the ability to monitor/measure the pumping activity of the natural heart if the VAD fails or if the VAD is turned off to test the capability or degree of recovery of the natural heart. It should be understood and appreciated that the elements and structure of the present sonomicrometric apparatus can be adapted and applied to other implantable biomedical devices to provide a sonomicrometer-based dimension-measurement data collection and evaluation system, as indicated in the following exemplary embodiments, as given below.

B. Inclusion of Dimension Measurement Capability in Pacemakers

Piezoelectric crystals (e.g., PZT or PVDF) are attached to pre-existing pacemaker pacing leads (so that the complexity of the implantation procedure is not increased), or the crystals are attached to separate leads so that they can be more appropriately positioned to measure specific cardiac dimension(s).

Previous patents issued to the assignee of the present application, Sonometrics Corporation, include the ability to sense bio-potentials through the existing metal plating on the crystal, so that the same wires can be used for ECG sensing and sonomicrometer operation with the appropriate multi-plexing circuits. These patents include U.S. Pat. No. 5,795, 298, issued Aug. 18, 1998, which is fully incorporated herein by reference.

A modification of the sonomicrometer measurement is the echo-reflection or single-element range-finder, where dimensions are measured from a single transducer to a selected reflection boundary. For example, this may result in the measurement of cardiac wall thickness at the site of transducer contact.

Pre-existing microcomputers inside the pacemaker may activate sonomicrometer (or range-finder) circuits continuously, or only during diagnostically relevant times to conserve battery power.

Multiple cardiac dimensions may be measured by increasing the number of transducers providing position data. During operation, the pacemaker may acquire cardiac dimensional data and compute items such as, but not limited to, actual heart beat rate, contractile amplitude, contractility, cardiac size, stroke volume and ejection fraction. This computed data is referred to as "computed parameters." The pacemaker uses the computed parameters to alter its functionality by, for example, deciding when pacing is, or is not, appropriate or indicated. Depending on the capabilities of the pacemaker and the clinical relevancy of the computed parameters, the computed parameters may be stored internally by the pacemaker so that a history or trend of these computed parameters can be clinically assessed. Computed parameters identifying a trend can again be used by the pacemaker to make decisions on when pacing is or is not, appropriate or indicated.

In cases where the ECG signal becomes compromised, the pacemaker may be switched into a mode where its' functionality is determined by the characteristics of the cardiac dimension signal(s) and/or the computed parameters.

C. Inclusion of Dimension Measurement Capability in Implantable Defibrillators The comments set forth above in section B also apply to an implantable defibrillator. Moreover, a defibrillator can use the cardiac dimensional data and/or the computed parameters to determine if there is a genuine need to apply a defibrillation shock. Once the shock is given, the subsequent cardiac dimensional data can provide invaluable information on post-shock cardiac contractility.

D. Use of Dimensional Measurements during Post-Operative Cardiac Monitoring

Two or more sonomicrometer transducers and/or one or more wall thickness transducers can be attached to the myocardium during an invasive heart procedure so that the resulting cardiac dimensional data and/or wall thickness data can be measured and parameters such as, but not limited to, heart rate contractile amplitude, contractility, cardiac size, stroke volume and ejection fraction can be computed. This information, and their trends, is displayed to clinicians during the procedure and also post-operatively by way of a bedside monitoring unit. These transducers are later detached from the myocardium and withdrawn though chest tubes that are normally in place post-operatively.

The state of the heart can be assessed by knowing the values of the various computed parameters and their trends. This information can be used to adjust drug doses and treatment protocols during recovery without employing more sophisticated diagnostic instruments such as echocardiography or Swan-Ganz catheterization. The continuous measurement of cardiac dimensional data during recovery can be tracked and alarms can be set to indicate poor cardiac function that can be acted upon immediately by medical staff.

E. Inclusion of Dimension Measurement Capability in Prosthetic Devices

Prosthetic devices that undergo shape changes in response to natural forces within the body are carefully designed to be durable for the life of the device. It is stated here that such devices would benefit from the inclusion of dimension-measurement transducers which would provide information on the degree of motion or flexing the :device is experiencing. Such information can be transmitted to a monitor outside the body during clinical evaluation of the device. Pending failure of the device, or indications that the device is functioning outside it's design limits, can be indicated by the data from the dimension measurement transducers, enabling medical personnel to take corrective action on the device. Examples of prosthetic devices that would benefit from the inclusion of dimension-measurement transducers are heart valves, vascular stents, and artificial joints.

F. Inclusion of Dimension Measurement Capability in Diagnostic, Therapeutic, and Surgical Instruments During certain medical procedures it is necessary to position or guide two or more instruments into a region of the body from different entry points or through different pathways. The addition of dimension measurement transducers to these instruments would provide a simple indication of their separation during insertion, manipulation, and positioning, allowing the clinician to position the devices appropriately.

An example would be the placement of a transjugular intra-hepatic portosystemic shunt. Additionally, a previously implanted dimension measurement transducer can act as a locator reference for diagnostic, therapeutic, or surgical instruments, enabling medical personnel to quickly and directly guide the instrument to the vicinity of the transducer.

The present invention has been described with reference to preferred embodiments. Obviously, modifications and alterations will occur to others upon a reading and understanding of this specification. It is intended that all such modifications and alterations be included insofar as they come within the scope of the appended claims or the equivalents thereof.

What is claimed:

1. A biomedical apparatus comprising:
   an implantable biomedical device for providing biomedical assistance to a body structure;
   a device controller for regulating operation of the biomedical device;
   a sonomicrometer arrangement, in contact with the body structure and in communication with the device controller, for ultrasonically measuring at least one physical dimension of the body structure and providing feedback information to the device controller, wherein the device controller regulates the operation of the biomedical device in response to the feedback information.

2. The biomedical apparatus of claim 1 wherein the sonomicrometer arrangement includes a plurality of ultrasonic transducers for respectively.sending and receiving ultrasonic signals.

3. The biomedical apparatus of claim 2 wherein the ultrasonic transducers are piezoelectric transducers for emitting ultrasound signals in a frequency range between about 1–10 MHz with an amplitude in an amplitude range of between about 1–50 mV.

4. The biomedical apparatus of claim 2 wherein the ultrasonic transducers are configured to measure the at least one physical dimension of the body structure during operation of the biomedical device.

5. The biomedical apparatus of claim 4 wherein the ultrasonic transducers are configured to measure a geometrical shape being at least one of 2-dimensional and 3-dimensional.

6. The biomedical apparatus of claim 2 wherein the ultrasonic transducers are encapsulated in a biocompatible material.

7. The biomedical apparatus of claim 2 wherein the ultrasonic transducers include a plurality of attachment rings, for affixing to a surface of the body structure.

8. The biomedical device of claim 1 wherein the implantable biomedical device is a ventricular assist device for providing auxiliary pumping support for a heart.

9. The biomedical apparatus of claim 1 wherein the device controller is part of an electronics module including a sonomicrometer control and a power supply.

10. The biomedical apparatus of claim 9 wherein sonomicrometer control includes a microprocessor that runs an embedded program that controls the operation of the sonomicrometer arrangement.

11. The biomedical apparatus of claim 10 wherein the embedded program causes the sonomicrometer arrangement to emit ultrasound pulses at a repetition rate of between about 50 Hz and about 500 Hz.

12. A biomedical method comprising:
   implanting a biomedical device for providing biomedical assistance to a body structure;
   ultrasonically measuring at least one physical dimension of the body structure;
   generating feedback information corresponding to the ultrasonically measured physical parameter; and
   regulating operation of the biomedical device in response to the feedback information.

13. The biomedical method of claim 12 wherein the step of ultrasonically measuring comprises measuring time of flight of an ultrasonic signal between a plurality of transducers.

14. The biomedical method of claim 12 wherein the step of ultrasonically measuring at least one physical parameter comprises measuring at least one physical dimension of the body structure during operation of the biomedical device.

15. The biomedical apparatus of claim 14 wherein the step of ultrasonically measuring at least one physical dimension comprises measuring a geometrical shape being at least one of 2-dimensional and 3-dimensional.

16. The biomedical method of claim 12 wherein the step of implanting comprises implanting a ventricular assist device for providing auxiliary pumping support for a heart.

17. The biomedical method of claim 16 wherein the step of ultrasonically measuring comprises measuring physical dimensions of at least a part of the heart to monitor occurrences of collapse and hyperdilation.

18. The biomedical method of claim 17 wherein the step of regulating comprises varying the ventricular assist device to prevent collapse and hyperdilation.

19. The biomedical method of claim 12 wherein the step of ultrasonically measuring comprises emitting ultrasound pulses at a repetition rate of between about 50 Hz and about 500 Hz.

* * * * *